(12) United States Patent
Ancel

(10) Patent No.: US 6,392,081 B1
(45) Date of Patent: May 21, 2002

(54) PROCESSES FOR PREPARING PESTICIDAL INTERMEDIATES

(75) Inventor: Jean-Erick Ancel, Saint Genis Laval (FR)

(73) Assignee: Aventis Agriculture Ltd., Ongar (GB)

( * ) Notice: Subject to any disclaimer, the term of this patent is extended or adjusted under 35 U.S.C. 154(b) by 0 days.

(21) Appl. No.: 09/673,801

(22) PCT Filed: Apr. 14, 1999

(86) PCT No.: PCT/EP99/02834

§ 371 Date: Dec. 22, 2000

§ 102(e) Date: Dec. 22, 2000

(87) PCT Pub. No.: WO99/54288

PCT Pub. Date: Oct. 28, 1999

(30) Foreign Application Priority Data

Apr. 20, 1998 (EP) .............................................. 98420069
Apr. 20, 1998 (EP) .............................................. 98420070

(51) Int. Cl.$^7$ ............................................ C07C 255/00
(52) U.S. Cl. ....................................................... 558/403
(58) Field of Search ................................. 558/394, 403

(56) References Cited

U.S. PATENT DOCUMENTS

| 4,824,960 A | 4/1989 | Gallenkamp et al. ....... 548/362 |
| 5,232,940 A | 8/1993 | Hatton et al. ............... 514/407 |

FOREIGN PATENT DOCUMENTS

| DE | 3612940 | * 10/1987 |
| EP | 0234119 | 9/1987 |
| EP | 0295117 | 12/1988 |
| WO | 97/32843 | 9/1997 |

OTHER PUBLICATIONS

Murahashi et al, *Chem. Abstracts*, vol. 53, No. 5, abstract No. 5163h, American Chemical Society, Columbus, Ohio (1959).

Schmidt et al, "Heilmittelchemische Studien in der heterocyclischen Reihe" *Helvetica Chimica Acta*, vol. 41, pp. 306–309, Verlag Helvetica Chimica Acta, Basel, Switzerland (1958).

Jachak et al, "Synthesis with nitriles XCI. Cyanoacetaldehyde—new synthetic applications of an old compound", *Monatshefte für Chemie*, vol. 124, No. 2, pp. 199–207, Springer–Verlag, Austria (1993).

March, *Advanced Organic Chemistry.*, 4th ed., p. 966, John Wiley & Sons, New York (1992).

Chemical Abstracts No. 5163h, XP002079282, vol. 53, No. 5, Murahashi et al., "The synthesis and some chemical properties", pp. 1689–1692, 1959.

Schmidt et al., "Heilmittelchemische Studien in der heterocyclischen Reihe", Helvetica Chimica Acta, vo. 41, Jan. 1, 1958, pp. 306–309.

\* cited by examiner

*Primary Examiner*—Alan L. Rotman
*Assistant Examiner*—Binta Robinson
(74) *Attorney, Agent, or Firm*—Burns, Doane, Swecker & Mathis, L.L.P.

(57) ABSTRACT

Processes for the preparation of a compound of the formula (I)

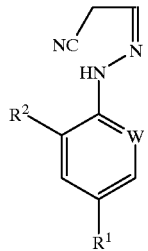

wherein W is nitrogen or —CR$^3$; R$^1$ is halogen, haloalkyl, haloalkoxy, R$^4$S(O)$_n$— or —SF$_5$; R$^2$ is hydrogen or halogen; R$^3$ is halogen; R$^4$ is alkyl or haloalkyl; and n is 0, 1 or 2.

28 Claims, No Drawings

PROCESSES FOR PREPARING PESTICIDAL INTERMEDIATES

This invention relates to novel processes for preparing intermediates (particularly 2-(arylhydrazino)succinonitrile compounds and 3-(arylhydrazono)propionitrile derivatives) useful in the preparation of pesticides.

European Patent Publication Nos. 0295117 and 0234119 describe the preparation of pesticidally active phenylpyrazole compounds and of 5-amino-1-aryl-3-cyanopyrazole intermediate compounds used in their synthesis.

Various methods for preparing these compounds are known. The present invention seeks to provide improved or more economical methods for the preparation of pesticides and the intermediate compounds useful in preparing them.

German Patent Publication No.3612940 discloses the preparation of 5-amino-1-arylpyrazole derivatives of general formula:

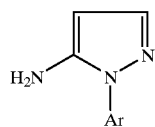

wherein Ar represents substituted phenyl or pyridyl, which can be used as intermediates in the preparation of compounds possessing herbicidal or pesticidal properties, by the reaction of arylhydrazine hydrochloride salts with formylacetonitrile sodium salt of formula:

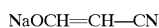

to give hydrazone compounds of general formula:

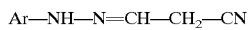

wherein Ar is as hereinbefore defined; which are then cyclised in the presence of a base.

However it may be desirable to obtain the hydrazone compounds in a pure form useful for their further conversion into pesticides. Known procedures may result in the formation of hydrazones which are contaminated with the cyclised 5-amino-1-arylpyrazole product.

The present applicants have surprisingly discovered a novel process for the preparation of the hydrazone compounds without cyclisation occurring. The hydrazone compounds may then be used either to provide a new method to prepare the 5-amino-1-arylpyrazole compounds, or in a novel process which involves addition of a cyanide to provide 2-(arylhydrazino)succinonitrile derivatives which may be further processed to provide important 5-amino-1-aryl-3-cyanopyrazole compounds which are valuable intermediates for the preparation of pesticides.

U.S. Pat. No. 4,824,960 describes the preparation of 5-amino-1-arylpyrazole derivatives of general formula:

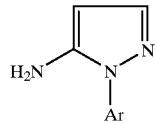

wherein Ar represents substituted phenyl or pyridyl, which can be used as intermediates in the preparation of compounds possessing herbicidal or pesticidal properties, by the reaction of arylhydrazines of formula:

wherein Ar is as hereinbefore defined, with acrylonitrile of formula:

in a first stage in the presence of a diluent and optionally a catalyst to give the 3-arylhydrazinopropionoitrile compounds of formula:

wherein Ar is as hereinbefore defined, followed by oxidation and cyclisation in a second process stage.

However if it is desired to perform an oxidation of the above 3-arylhydrazinopropilonitriles (without cyclisation to the 5-amino-1-arylpyrazoles) in order to obtain 3-arylhydrazonopropionitriles, which may then be further processed to provide important 5-amino-1-aryl-3-cyanopyrazole compounds which are valuable intermediates in the preparation of pesticides, a different process must be employed.

The present invention accordingly provides a process (A) for the preparation of a compound of formula (I):

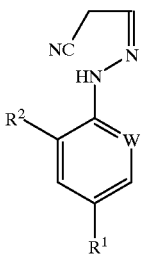

(I)

wherein W represents nitrogen or —$CR^3$;

$R^1$ represents halogen, haloalkyl (preferably trifluoromethyl), haloalkoxy (preferably trifluoromethoxy), $R^4S(O)_n$—, or $SF_5$;

$R^2$ represents hydrogen or halogen (for example chlorine or bromine);

$R^3$ represents halogen (for example chlorine or bromine);

$R^4$ represents alkyl or haloalkyl; and n represents 0,1 or 2; which process comprises the reaction of a compound of formula (II):

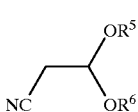

(II)

wherein $R^5$ and $R^6$ independently represent alkyl or together represent an alkylene chain containing two or three carbon atoms, with an acid addition salt of an arylhydrazine compound of formula (III):

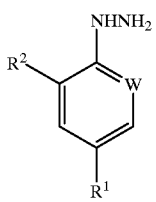

(III)

wherein $R^1$, $R^2$ and W are as hereinbefore defined. Compounds of formula (I) may exist as a mixture of syn and anti isomers or as individual isomers.

Unless otherwise specified in the present specification 'alkyl' means straight- or branched-chain alkyl having from one to six carbon atoms (preferably one to three). Unless otherwise specified 'haloalkyl' and 'haloalkoxy' are straight- or branched-chain alkyl or alkoxy respectively having from one to six carbon atoms (preferably one to three) substituted by one or more halogen atoms selected from fluorine, chlorine or bromine.

Generally $R^5$ and $R^6$ in formula (II) represent the same alkyl group, preferably methyl or ethyl.

The acid addition salts of the compounds of formula (III) are preferably the salts formed from strong acids such as mineral acids, for example sulphuric acid, or preferably hydrochloric acid. Generally the salts are pre-formed but may optionally be generated in situ. The reaction may be conducted in a polar or a non-polar solvent in the presence of water. Examples of polar solvents include water; alcohols such as methanol or ethanol; nitriles such as acetonitrile; N-methylpyrrolidone or sulphoxides such as dimethyl sulphoxide. Examples of non-polar solvents include chlorinated hydrocarbons, preferably carbon tetrachloride; and hydrocarbons such as cyclohexane. The reaction temperature is generally from 20° C. to 100° C., preferably from 50° C. to 90° C. Equimolar amounts of the compounds of formula (II) and (III) are generally employed. The amount of water which may be present is from a catalytic amount to a large excess.

In formulae (I), (III) and in the formulae depicted hereinafter, preferred values of the symbols are as follows:

$R^1$ represents haloalkyl (preferably trifluoromethyl), haloalkoxy (preferably trifluoromethoxy) or —$SF_5$;

W represents —$CR^3$; and $R^3$ represents halogen;

A most preferred compound of formula (I) is 3-(2,6-dichloro-4-trifluoromethylphenylhydrazono)propionitrile.

A further preferred compound of formula (I) is 3-(2-chloro-4-trifluoromethylphenylhydrazono)propionitrile.

Compounds of formula (II) and (III) are generally known in the literature.

The process of the invention is characterised by a number of advantages. Thus, it seeks to enable 3-arylhydrazonopropionitrile compounds of formula (I) to be obtained in high yield from readily available starting materials. Furthermore the reaction can be very simple and economical to perform, and product isolation is very straightforward. Furthermore the compounds of formula (I) can be obtained without substantial cyclisation occurring.

According to a further feature of the present invention there is provided a process (B) for the preparation of a compound of formula (I), wherein W, $R^1$ and $R^2$ are as hereinbefore defined, which comprises the reaction of a compound of formula (IV):

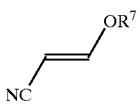

(IV)

wherein $R^7$ represents alkyl (preferably methyl or ethyl), with a compound of formula (III), wherein $R^1$, $R^2$ and W are as hereinbefore defined. The reaction conditions which are generally employed are the same as those used for the above preparation of a compound of formula (I) from the reaction of a compound of formula (II) with an acid addition salt of a compound of formula (III).

Compounds of formula (IV) are generally known in the literature.

According to a further feature of the present invention there is provided a process (C) for the preparation of a compound of formula (I) wherein W, $R^1$ and $R^2$ are as hereinbefore defined; which process comprises the oxidation of a compound of formula (V):

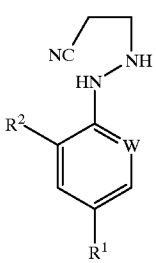

(V)

wherein $R^1$, $R^2$ and W are as hereinbefore defined.

Suitable oxidants for the above reaction to form compounds of formula (I) include quinones such as benzoquinone, peroxides such as hydrogen peroxide, hypohalites such as sodium hypochlorite; or preferably a metal salt or oxide for example cupric chloride or mercuric oxide. The oxidation is generally conducted in a solvent. Solvents suitable for use include aromatic halogenated or non-halogenated hydrocarbons such as toluene or chlorobenzene, nitriles such as acetonitrile or amides such as N,N-dimethylformamide. The reaction temperature is generally from about 20° C. to about 150° C., and preferably from about 50° C. to about 100° C.

The molar ratio of oxidant to compound of formula (V) is generally from 0.01:1 to 5:1, preferably from 1:1 to 3:1.

According to a further feature of the present invention there is provided a process (D) for the preparation of a compound of formula (VI):

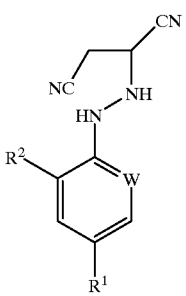

(VI)

wherein $R^1$, $R^2$ and W are as hereinbefore defined; which process comprises the reaction of a compound of formula (I) wherein $R^1$, $R^2$ and W are as hereinbefore defined, with a source of hydrogen cyanide. Compounds of formula (VI) may exist in the R- and S- forms or as mixtures thereof.

The source of hydrogen cyanide may be hydrogen cyanide gas itself, when the reaction is optionally performed in the presence of a base, for example pyridine; but it is preferably prepared in situ (to avoid the direct use of hydrogen cyanide) from a metal cyanide salt (generally an alkali metal cyanide, for example sodium cyanide or potassium cyanide),in the presence of an acid. Suitable acids include organic acids such as aliphatic carboxylic acids for example acetic acid, or halogenated aliphatic carboxylic acids for example chloroacetic acid or trifluoroacetic acid; sulphonic acids such as benzenesulphonic acid, 4-toluenesulphonic acid or methanesulphonic acid; or inorganic acids such as hydrochloric acid or sulphuric acid.

Alternative sources of hydrogen cyanide (which may be generated in situ) are trimethylsilylcyanide in water, or a mixture of trimethylsilylcyanide and a Lewis acid, for example tin (IV) tetrachloride, in a solvent such as dichloromethane or tetrahydrofuran, at a temperature of from 20° C. to 100° C., preferably from 30° C to 60° C. The reaction is preferably performed under increased pressure which increases the speed of the reaction.

The preparation of compounds of formula (VI) from compounds of formula (I) may be effected in a polar or a non-polar solvent. Examples of polar solvents which may be used include water; alcohols such as methanol or ethanol; N,N-dimethylformamide; dimethylsulphoxide; or alkanoic acids such as acetic acid. Examples of non-polar solvents include hydrocarbons such as hexane, or ethers such as tetrahydrofuran, dioxane or dialkyl ethers such as diethyl ether; or nitriles such as acetonitrile. When a metal cyanide salt is used in the presence of an acid, the preferred solvent is water or a mixture of water with a water miscible solvent. An equimolar amount or excess of the cyanide source may be employed, generally from 1 to 4 molar equivalents are used. The reaction temperature is generally from 0° C. to 100° C., preferably from 20° C. to 50° C.

Most preferably the compound of formula (VI) is 2-(2,6-dichloro-4-trifluoromethylphenylhydrazino)succinonitrile.

A further preferred compound of formula (VI) is 2-(2-chloro-4-trifluoromethylphenylhydrazino)succinonitrile.

According to a further feature of the invention processes (A) and (D) can be combined to prepare a compound of formula (VI) from a compound of formula (III).

According to a further feature of the invention processes (B) and (D) can be combined to prepare a compound of formula (VI) from a compound of formula (III).

According to a further feature of the invention processes (C) and (D) can be combined to prepare a compound of formula (VI) from a compound of formula (V).

According to a further feature of the invention the above combination of processes (C) and (D) can be combined with an additional process step (E), which comprises the reaction of an arylhydrazine compound of formula (III) wherein $R^1$, $R^2$ and W are as hereinbefore defined; with acrylonitrile of formula (VII):

$$NC-CH=CH_2 \quad (VII)$$

to give a compound of formula (V) as defined above.

Compounds of formula (VII) are known.

The compounds of formula (I) obtained by process (A) or (B) or (C) of the invention may be used in the preparation of pesticidally active 5-amino-1-arylpyrazole derivatives of formula (VIII) according to the following reaction scheme:

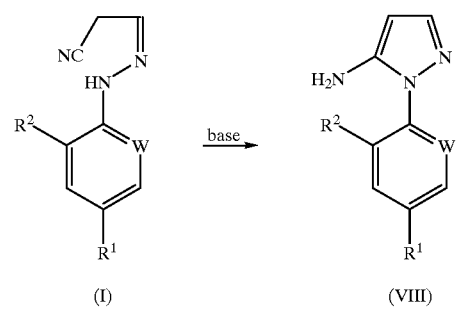

wherein $R^1$, $R^2$ and W are as hereinbefore defined.

The compounds of formula (VI) obtained by the process (D) of the invention are particularly useful in the preparation of pesticidally active 5-amino-1-aryl-3-cyanopyrazole derivatives of formula (IX) obtained from intermediate compounds of formula (X) and (XI) according to the following reaction scheme:

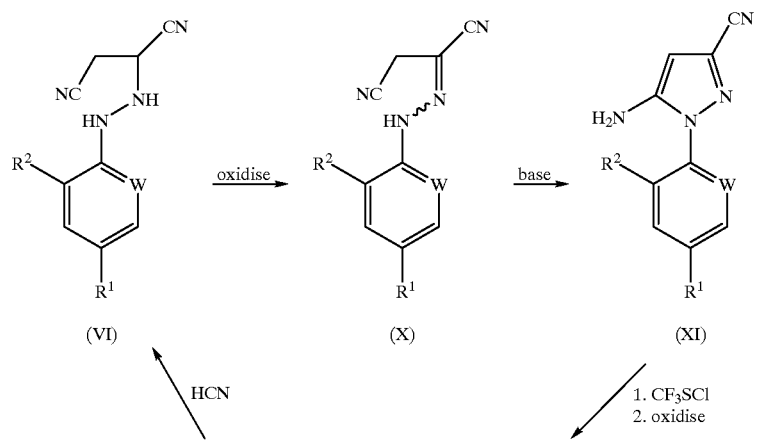

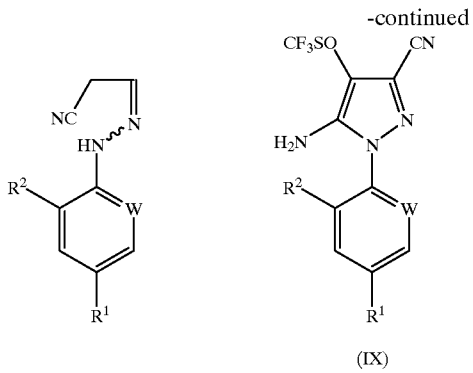

(IX)

wherein $R^1$, $R^2$ and W are as hereinbefore defined.

Compounds of formula (X) may be prepared by the oxidation of compounds of formula (VI). Suitable oxidants for the reaction include quinones such as benzoquinone, peroxides such as hydrogen peroxide, hypohalites such as sodium hypochlorite, or an alkali metal hydroxide such as sodium hydroxide in the presence of air, or preferably a metal salt or oxide for example cupric chloride or mercuric oxide. The reaction is generally conducted in a solvent. Solvents suitable for use include aromatic halogenated or non-halogenated hydrocarbons such as toluene or chlorobenzene, nitrites such as acetonitrile or amides such as N,N-dimethylformamide. The reaction temperature is generally from about 20 to about 150° C., and preferably from about 50 to about 100° C. The molar ratio of oxidant to compound of formula (VI) is generally from 0.01:1 to 5:1, preferably from 1:1 to 3:1.

Compounds of formula (XI) may be prepared from compounds of formula (X) according to known methods.

The following non-limiting examples illustrate the invention. NMR spectra are recorded using deuterochloroform as solvent.

EXAMPLE 1

Preparation of 3-(2,6-Dichloro-4-trifluoromethylphenylhydrazono)propionitrile from 3,3-Dimethoxypropionitrile 2,6-Dichloro-4-trifluoromethylphenylhydrazine hydrochloride was prepared by bubbling hydrogen chloride gas into an ether solution of 2,6-dichloro-4-trifluoromethylphenylhydrazine and filtration of the hydrochloride salt which was obtained in quantitative yield. Carbon tetrachloride (5 ml) and 3,3-dimethoxypropionitrile (141 microlitres) were added successively to a solution of the above 2,6-dichloro-4-trifluoromethylphenylhydrazine hydrochloride (0.349 g) in water (5 ml) was heated at 75° C. for 10 hours. The cooled mixture was extracted (dichloromethane), washed (water), dried (magnesium sulphate) and evaporated to give the title compound (0.358 g), NMR 3.37(d,2H), 7.03(t,1H), 7.5(s,2H), 7.75(s,1H). The yield was 98%.

EXAMPLE 2

Preparation of 3-(2,6-Dichloro-4-trifluoromethylphenylhydrazono)propionitrile from 3,3-Dimethoxypropionitrile A mixture of 2,6-dichloro-4-trifluoromethylphenylhydrazine (1.8 g) and hydrochloric acid (4 ml of 2N, 1 equivalent) was heated to 80° C. under an inert atmosphere. 3,3-Dimethoxypropionitrile (912 microlitres, 1 equivalent) was added in one portion and the mixture heated at 80° C. for 2 hours, cooled, extracted (dichloromethane), washed (water), dried (magnesium sulphate) and evaporated. The residue was purified by chromatography on silica gel eluting with dichloromethane to give the title compound (1.4 g), NMR 3.37(d,2H), 7.03 (t,1H), 7.5(s,2H), 7.75(s,1H). The yield was 59%.

EXAMPLE 3

Preparation of 3-(2,6-Dichloro-4-trifluoromethylphenylhydrazono)propionitrile from 3-Methoxy-aclryloitrile By proceeding according to Example 1 but replacing the 3,3-dimethoxypropionitrile by 3-methoxy-acrylonitrile there was obtained, after purification by chromatography on silica gel eluting with dichloromethane, the title compound, NMR 3.37(d,2H), 7.03(t,1H), 7.5(s,2H), 7.75(s,1H). The yield was 63%.

EXAMPLE 4

Preparation of 2-(2,6-Dichloro-4-trifluoromethylphenylhydrazino)succinonitrile 2-(2, 6-Dichloro-4-trifluoromethylphenylhydrazono) succinonitrile (0.296 g, 1 mmol), sodium cyanide (0.196 g, 4 equivalents), water (1 ml) and acetic acid (5 ml) were added successively to a sealed tube. After reacting for 40 hours at 20° C. the mixture was added to saturated sodium bicarbonate solution, extracted (dichloromethane), washed (water), dried (magnesium sulphate) and evaporated to give a mixture which contained 40% of the desired title compound, NMR 3.1 (m,2H), 4.5(m,1H), 5.89(m, 1H), 6.94(d,1H), 7.71(s,2H), together with 60% of unchanged starting hydrazone.

EXAMPLE 5

Preparation of 3-(2,6-Dichloro-4-trifluoromethylphenylhydrazono)propionitrile from 3-(2,6-Dichloro-4-trifluoromethylphenylhydrazino) propionitrile Cupric chloride (0.673 g, 2.5 equivalents) was added in one portion to a solution of 3-(2,6-dichloro-4-trifluoromethylphenylhydrazino)propionitrile (0591 g, 2 mmol) in chlorobenzene, and the mixture heated at 65° C. for 50 minutes. The reaction was judged to be complete and was cooled, washed (water), dried (magnesium sulphate), evaporated and separated by chromatography on silica gel to give 3-(2,6-dichloro-4-trifluoromethylphenylhydrazono) propionitrile, NMR 3.37(d,2H), 7.03(t,1H), 7.5(s,2H), 7.75(s,1H) (35% yield), and 3-(2,6-dichloro-4-trifluoromethylphenylazo)propionitrile, NMR 3.0(t,2H), 4.6(t,2H), 7.6(s,2H) (60% yield).

EXAMPLE 6

Preparation of 2-(2,6-dichloro-4-trifluoromethylphenylhydrazino)succinonitrile 2-(2,6-Dichloro-4-trifluoromethylphenylhydrazono)succinonitrile (0.296 g, 1 mmol), sodium cyanide (0.196 g, equivalents), water (1 ml) and acetic acid (5 ml) were added successively to a tube, which was sealed and reacted at 20° C. for 40 hours. The mixture was added to saturated sodium bicarbonate solution, extracted (dichloromethane), washed (water), dried (magnesium sulphate) and evaporated to give a mixture which contained 40% of the desired title compound, NMR 3.1 (m,2H), 4.5(m,1H), 5.89(m,1H), 6.94 (d,1H), 7.71(s,2H), together with 60% of unchanged starting hydrazone.

REFERENCE EXAMPLE i) Preparation of 2-(2,6-Dichloro-4-trifluoromethylphenylhydrazono)succinonitrile A mixture of 2-(2,6-dichloro-4-trifluoromethylphenylhydrazino)succinonitrile (0.323 g) and cupric chloride (0.175 g) was heated in chlorobenzene at 60° C. for 6 hours. After filtration and evaporation the title compound and 5-amino-3-cyano-1-(2,6-dichloro-4-trifluoromethylphenyl)pyrazole were obtained as a 7:1 mixture. Column chromatography on silica gel eluting with dichloromethane gave the pure title compound, obtained as a mixture of syn and anti isomers, NMR (anti isomer) 3.6(s,2H), 7.57(s,2H), 8.82(s,1H, exchangeable with $D_2O$), NMR (syn isomer) 3.56(s,2H), 7.59(s,2H), 8.27(s,1H, exchangeable with $D_2O$).

ii) Preparation of 5-Amino-3-cyano-1-(2,6-dichloro-4-trifluoromethylphenyl)pyrazole Ammonia (20 microlitres of an 8% ammonia solution in water) was added to a mixture of the above 2-(2,6-dichloro-4-trifluoromethylphenylhydrazono)-succinonitrile (0.077 g) in ethanol (1 ml) and water (0.2 ml) at 0° C. After 10 minutes the mixture was extracted (dichloromethane) and evaporated to give 5-amino-3-cyano-1-(2,6-dichloro-4-trifluoromethylphenyl)pyrazole (0.076 g, 97% yield) Purity 98% (by hplc).

What is claimed is:

1. A process for the preparation of a compound of formula (I):

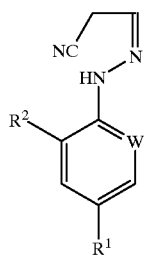

(I)

wherein W represents $CR^3$;

$R^1$ represents halogen, haloalkyl, haloalkoxy, $R^4S(O)_n$—, or —$SF_5$;

$R^2$ represents hydrogen or halogen;

$R^3$ represents halogen;

$R^4$ represents alkyl or haloalkyl; and n represents 0, 1 or 2; which process comprises:

(A) reacting a compound of formula (II):

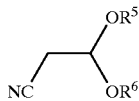

(II)

wherein $R^5$ and $R^6$ independently represent alkyl or together represent an alkylene chain having two or three carbon atoms, with an acid addition salt of an arylhydrazine compound of formula (III):

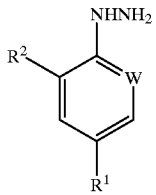

(III)

wherein $R^1$, $R^2$ and W are as hereinbefore defined; or (B) reacting a compound of formula (IV):

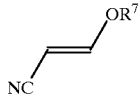

(IV)

wherein $R^7$ represents alkyl, with an acid addition salt of an aryl hydrazine compound of formula (III), wherein $R^1$, $R^2$ and W are as hereinbefore defined; or (C) oxidizing a compound of formula (V):

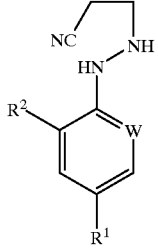

(V)

wherein $R^1$, $R^2$ and W are as hereinbefore defined with an oxidant.

2. A process according to claim 1 wherein, in process (A), $R^5$ and $R^6$ each represent methyl or ethyl.

3. A process according to claim 1 wherein, in process (A) or (B), the acid addition salt of the compound of formula (III) is the salt formed from a strong acid.

4. A process according to claim 1 wherein, in process (A) or (B), water is present.

5. A process according to claim 1 wherein, in process (C), the oxidant is a metal salt or oxide.

6. A process according to claim 1 wherein, in process (C), the process is conducted in a solvent.

7. A process according to claim 1 wherein, in process (C), the molar ratio of oxidant to compound of formula (V) is from 0.01:1 to 5:1.

8. A process according to claim 1, wherein process (C) is followed by reacting a compound of formula (I) with a source of hydrogen cyanide to prepare a compound of formula (VI)

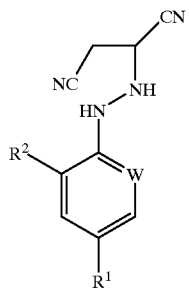

(VI)

wherein $R^1$, $R^2$ and W are as defined in claim 1.

9. A process according to claim 1 wherein, in process (C), the compound of formula (V) is prepared by reacting a compound of formula (III) wherein $R^1$, $R^2$ and W are as defined in claim 1, with acrylonitrile of formula (VII):

NC—CH=CH$_2$ (VII).

10. A process according to claim 1, wherein $R^1$ represents haloalkyl, haloalkoxy or —SF$_5$;
W represents —CR$^3$; and R$^3$ represents halogen.

11. A process according to claim 1, wherein $R^1$ represents trifluoromethyl, W represents —CR$^3$, and $R^2$ and $R^3$ represent chlorine.

12. A process according to claim 1, wherein $R^1$ is haloalkyl or haloalkoxy.

13. A process according to claim 12, wherein $R^1$ is trifluoromethyl or trifluoromethoxy.

14. A process according to claim 1, wherein $R^2$ is halogen.

15. A process according to claim 14, wherein $R^2$ is chlorine or bromine.

16. A process according to claim 1, wherein $R^3$ is chlorine or bromine.

17. A process according to claim 1, wherein, in process (C), $R^7$ is methyl or ethyl.

18. A process according to claim 5, which is conducted in a solvent.

19. A process according to claim 5, wherein the molar ratio of oxidant to compound of formula (V) is from 0.01:1 to 5:1.

20. A process according to claim 6, wherein the molar ratio of oxidant to compound of formula (V) is from 0.01:1 to 5:1.

21. A process according to claim 7, wherein the molar ratio of oxidant to compound of formula (V) is from 1:1 to 3:1.

22. A process according to claim 19, wherein the molar ratio of oxidant to compound of formula (V) is from 1:1 to 3:1.

23. A process according to claim 20, wherein the molar ratio of oxidant to compound of formula (V) is from 1:1 to 3:1.

24. A process according to claim 5, wherein the compound of formula (V) is prepared by reacting a compound of formula (III) wherein $R^1$, $R^2$ and W are as defined in claim 5, with acrylonitrile of formula (VII):

NC—CH=CH$_2$ (VII).

25. A process according to claim 6, wherein the compound of formula (V) is prepared by reacting a compound of formula (III) wherein $R^1$, $R^2$ and W are as defined in claim 6, with acrylonitrile of formula (VII):

NC—CH=CH$_2$ (VII).

26. A process according to claim 7, wherein the compound of formula (V) is prepared by reacting a compound of formula (III) wherein $R^1$, $R^2$ and W are as defined in claim 7, with acrylonitrile of formula (VII):

NC—CH=CH$_2$ (VII).

27. A process according to claim 8, wherein the compound of formula (V) is prepared by reacting a compound of formula (III) wherein $R^1$, $R^2$ and W are as defined in claim 14, with acrylonitrile of formula (VII):

NC—CH=CH$_2$ (VII).

28. A process according to claim 1, wherein $R^1$ represents trifluoromethyl, trifluoromethoxy or —SF$_5$; W represents —CR$^3$; and R$^3$ represents halogen.

* * * * *